US010813967B2

(12) United States Patent
Deshpande et al.

(10) Patent No.: US 10,813,967 B2
(45) Date of Patent: Oct. 27, 2020

(54) COMPOSITION OF OILY, PUNGENT AND ODORIFEROUS SUBSTANCES AND A PROCESS OF PREPARATION THEREOF

(71) Applicant: OmniActive Health Technologies Limited, Mumbai, Maharashtra (IN)

(72) Inventors: Jayant Deshpande, Charlottetown (CA); Girish Achliya, Thane (IN); Pravin Nalawade, Thane (IN); Prakash Bhanuse, Thane (IN); Swapnil Khamborkar, Thane (IN)

(73) Assignee: OmniActive Health Technologies Limited, Mumbai, Maharashtra (IN)

( * ) Notice: Subject to any disclaimer, the term of this patent is extended or adjusted under 35 U.S.C. 154(b) by 70 days.

(21) Appl. No.: 14/463,249

(22) Filed: Aug. 19, 2014

(65) Prior Publication Data
US 2015/0209400 A1 Jul. 30, 2015

(30) Foreign Application Priority Data
Jan. 30, 2014 (IN) .......................... 327/MUM/2014

(51) Int. Cl.
| | | |
|---|---|---|
| *A61K 36/81* | (2006.01) | |
| *A23L 33/125* | (2016.01) | |
| *A23L 5/00* | (2016.01) | |
| *A61K 31/165* | (2006.01) | |
| *A61K 9/16* | (2006.01) | |
| *A23L 2/56* | (2006.01) | |
| *A23L 2/58* | (2006.01) | |
| *A23P 10/30* | (2016.01) | |
| *A23L 27/00* | (2016.01) | |
| *A23L 27/10* | (2016.01) | |
| *A23L 33/105* | (2016.01) | |
| *A23L 29/30* | (2016.01) | |
| *A23L 29/262* | (2016.01) | |
| *A23L 27/18* | (2016.01) | |
| *A23L 27/16* | (2016.01) | |

(52) U.S. Cl.
CPC ............. *A61K 36/81* (2013.01); *A23L 2/56* (2013.01); *A23L 2/58* (2013.01); *A23L 5/00* (2016.08); *A23L 27/10* (2016.08); *A23L 27/72* (2016.08); *A23L 33/105* (2016.08); *A23L 33/125* (2016.08); *A23P 10/30* (2016.08); *A61K 9/1652* (2013.01); *A61K 9/1694* (2013.01); *A61K 31/165* (2013.01); *A23L 27/16* (2016.08); *A23L 27/18* (2016.08); *A23L 29/262* (2016.08); *A23L 29/30* (2016.08); *A23L 29/37* (2016.08); *A23V 2002/00* (2013.01)

(58) Field of Classification Search
None
See application file for complete search history.

(56) References Cited

U.S. PATENT DOCUMENTS

| | | |
|---|---|---|
| 5,273,754 A | 12/1993 | Mann |
| 6,201,014 B1 | 3/2001 | Gardiner |
| 6,326,031 B1 | 12/2001 | Hsia et al. |
| 2007/0264411 A1 | 11/2007 | Ito et al. |
| 2008/0008770 A1 | 1/2008 | Astrup et al. |
| 2008/0268092 A1 | 10/2008 | Dacanay |
| 2011/0020443 A1* | 1/2011 | Liu ................ A61K 31/191 424/464 |
| 2011/0097395 A1* | 4/2011 | Babul ............. A61K 9/1635 424/451 |

FOREIGN PATENT DOCUMENTS

| | | |
|---|---|---|
| CN | 102429871 | 5/2012 |
| IN | 254661 | 12/2012 |
| KR | 20080030844 | * 4/2008 |
| WO | WO 2004/056336 | * 7/2004 |

(Continued)

OTHER PUBLICATIONS

"Omniactive's Dr. Deshpande to Discuss Latest Capsimax™ Research at SupplyExpo", OmniActive Health Technologies *Engredea News & Analysis*, Feb. 16, 2009, 3 pages and can be found at hups://newhope360.com/health/omniactives-dr-deshpande-discuss-latest-capsimax-research-supplyexpo.

Verma et al., "Current Status of Drug Delivery Technologies and Future Directions", Pharmaceutical Technology On-Line, 25(2), 14 pages, 2001 and can be found at http://www.pharmanet.com/br/pdf/drugdelivery.pdf.

(Continued)

*Primary Examiner* — David J Blanchard
*Assistant Examiner* — Sarah J Chickos
(74) *Attorney, Agent, or Firm* — Hamre, Schumann, Mueller & Larson, P.C.

(57) ABSTRACT

A composition of oily, pungent and odoriferous substances and a process for preparation thereof are described, in particular an extended and sustained release of a stable, free flowing, solid composition of one or more of substances such as *capsicum*, black pepper, ginger, mustard, cinnamon, garlic, onion, paprika, turmeric and the like, extracts thereof, and/or components thereof, and a process for preparation thereof are described. For example, compositions comprise a substance such as *capsicum* containing capsaicinoid components, which include for example capsaicin, dihydrocapsaicin, and/or nor-dihydro-capsaicin. The composition can eliminate the discomfort by facilitating intestinal absorption of the active ingredient and thereby minimizing/eliminating the discomfort caused by the residual unabsorbed active ingredient, and can be particularly suitable for formulating into consumable dry syrups, tablets, capsules, liquid syrups, health drinks, diet drinks, fruit juices, and/or soft drinks, which can be useful in reduction of body weight.

11 Claims, 3 Drawing Sheets

(56) References Cited

FOREIGN PATENT DOCUMENTS

WO    WO 2007/096902    8/2007

OTHER PUBLICATIONS

International Search Report for Application No. PCT/IB2014/001569, dated Jan. 26, 2015, 4 pages.
Written Opinion for International Application No. PCT/IB2014/001569, dated Jan. 26, 2015, 6 pages.

\* cited by examiner

COMPOSITION OF OILY, PUNGENT AND ODORIFEROUS SUBSTANCES AND A PROCESS OF PREPARATION THEREOF

FIELD OF THE INVENTION

The present invention generally relates to a composition of oily, pungent and odoriferous substances and a process for preparation thereof. The present invention particularly relates to an extended and sustained release of a stable, free flowing, solid composition of one or more of pungent substances such as *capsicum*, black pepper, ginger, mustard, cinnamon, garlic, onion, paprika, turmeric and the like, extracts thereof, and/or components thereof. For example, the compositions comprise a substance such as *capsicum* containing capsaicinoid components, which can include for example one or more of capsaicin, dihydro-capsaicin, and/or nor-dihydro-capsaicin, and a process for preparation of the composition.

BACKGROUND OF THE INVENTION

In modern times, obesity is identified as a cause of serious complications during diseases such as diabetes and myocardial infarction. It is also a major factor for a number of diseases, including coronary heart disease (CHD), hypertension, non-insulin dependent diabetes mellitus, pulmonary dysfunction, osteoarthritis and certain types of cancer. Serious attention is being given for weight reduction and anti-oxidant, protective effects. Factors suggested as being related to the development of obesity are decreased physical activity and increased energy intake, especially fat intake. Weight loss and loss of body fat can thus be achieved by reducing energy intake and/or increasing energy expenditure.

The limited long-term effectiveness of conventional weight management (dietary intervention, physical activity and behavioral therapy) requires alternative weight-reduction strategies. A rapidly growing therapeutic area, largely embraced by the general public, is the use of natural herbal supplements. A wide range of herbal products are currently being marketed as weight-loss agents. These include various compounds of spice and herbal origin, such as red hot peppers (*Capsicum* species) or *Capsicum* Extracts (for weight management) or Cinnamon, Cinnamon extracts (for blood glucose management), Garlic oil and extracts (for cholesterol management) Mustard oil and turmeric derivatives (as anti-oxidant) etc. The use of herbal or plant based products have gained importance because of their safety, availability and absence of after effects.

Capsaicin is the pungent principle associated with cayenne/red pepper. It is a prominent chemical entity in plants of *Capsicum* genus which includes chili peppers, red pepper, and paprika. Capsaicin is actually a class of compounds of branched and straight chain alkyl vannilamides. The anti-microbial and analgesic properties of capsaicin have been known for centuries. Other human studies and animal models report the weight reduction benefits of capsaicin. These studies show diet-induced thermo genesis (i.e., an increase in energy expenditure in the body) and a reduction in appetite levels (shown by decreased cumulative food intake) after consumption of Capsaicin from red peppers or their concentrated extracts. It also shows a beneficial reduction in body mass, percentage body fat, waist circumference, and a desirable reduction in levels of critical markers of weight maintenance such as blood glucose, insulin, triacylglycerol and leptin. All these point towards the immense potential for nutritionists to incorporate *Capsicum* and its active compounds. Capsaicinoids in dietary formulations curb excess appetite, prevent weight gain and facilitate weight loss inducing behavior.

Due to the enhanced awareness of weight loss properties of *capsicum* or *capsicum* extract or capsaicin and their ability to reduce complications of excessive fat in diseases such as diabetes, there is a great demand for such actives which not only aim for weight reduction but also which are cheap, based on herbs and natural products and which have no side effects during their prolonged continuous use.

These compounds are associated with reducing energy intake, enhancing energy expenditure and facilitating weight control. However, effective dosage forms require minimum capsaicinoids levels of much greater than 10-20,000 Scoville Heat Units (SHU) to be delivered to the consumer in a non-bulky form, and for that the ingredients which need to be used as starting material in manufacturing systems are found at heat levels typically as high as 250,000-10, 00,000 SHU (i.e. 25-50 times "hotter" than what is to be "consumed" by the end user).

Furthermore, substances such as *capsicum* or *capsicum* extracts or capsaicin, mustard oil, turmeric, onions and the like are oily, irritating and odoriferous. These substances are also extremely pungent and irritating to the skin and mucus membrane. They cannot be easily converted in to dosage forms such as tablets/capsules due to their intense pungency and skin irritation properties. Converting them into dosage forms such as tablets or capsules was found to be impractical. In addition, the operators working on the granulation or tablet compression machine could not tolerate the intense pungency arising out of the very fine dust particles of *capsicum*.

In order to find a satisfactory solution to the persisting problems, there was a need to develop a novel technology which could not only facilitate their administration at doses adequate for nutritional and health benefits but which also addresses the handling difficulties of such pungent and irritating substances during formulation and manufacture.

This discomfort can be eliminated by providing a composition that can facilitate complete intestinal absorption of the active ingredient and thereby minimize/eliminate the discomfort caused by residual unabsorbed active ingredient. Accordingly, there exists a need to provide a composition comprising oily, pungent and odoriferous substance for weight reduction providing for extended and sustained release of the active ingredient.

Various ready to use formulations are available in the market for reduction or weight loss reduction.

US 2007/0264411 provides a process of producing a capsaicinoid containing food and drink with superior stability. US 2007/0264411 discloses an emulsion composition comprising capsaicinoid compound and a process thereof. The process described in US 2007/0264411 entails blending an oil phase containing capsaicinoid compound with an aqueous phase and an emulsifier. The capsaicinoids mentioned in US 2007/0264411 are non-pungent and are different from the pungent components of red pepper, capsaicinoids.

GB 2469658 provides a beverage containing capsaicinoid. GB 2469658 discloses a beverage comprising a flavored component, water and capsaicinoid composition extracted from *Capsicum* as a heat providing component and a process for its preparation.

US 2008/0008770 provides a composition for weight reduction in capsule form with effective amount of capsaicin, L-tyrosine, supplemental caffeine and green tea extract containing catechin and caffeine.

U.S. Pat. No. 6,326,031 discloses nutritional supplements to the human diet used to increase levels of HDL and decreases levels of O-LDL, cholesterol, and triglycerides in the human plasma. The nutritional supplement contains a combination of fish oil, garlic, rutin and capsaicin. It further includes methods of preparing the nutritional supplements.

US 2008/0268092 provides a nutritional supplement to reduce body fat which comprises a synergistic combination of vanilloid receptor subtype 1 agonist and methylxanthine.

U.S. Pat. No. 5,273,754 discloses an appetite suppressant composition for oral administration. The composition includes a heating and a cooling carminative substance, and may also include an amino acid and an anxiolytic substance. Also disclosed are methods for decreasing appetite by oral administration of the appetite suppressant composition, and for manufacture of the appetite suppressant composition.

IN254661 provides a free flowing solid composition of oily or pungent and odoriferous substances and a process for their preparation thereof. It particularly discloses solid compositions such as beadlets which are suitable for formulating into tablets, capsules, blended powders, licaps, ointments, pastes, lotions, liniments, mouthwashes, and gargles etc.

While the disclosures provide a wide range of processes and formulations for the use of *capsicum* and other weight controlling agents, the processes in the references are not adequate for reducing the irritation caused by these substances. Further, these disclosures do not provide an extended and sustained release formulation which eliminates the discomfort by facilitating complete intestinal absorption of the active ingredient and thereby minimizing/eliminating the discomfort caused by the residual unabsorbed active ingredient. The extended and sustained release, stable, free flowing, solid microspheres of the present invention are particularly suitable for formulating into consumable dry syrups, tablets, capsules, liquid syrups, health drinks, diet drinks, fruit juices, soft drinks and the like which are useful in reduction of body weight.

OBJECTIVES OF THE INVENTION

Such a need is appropriately addressed by the present invention which provides an extended and sustained release of a stable, free flowing, solid composition of one or more pungent substances such as *capsicum*, black pepper, ginger, mustard, cinnamon, garlic, onion, paprika, turmeric and the like, extracts thereof, and/or components thereof, and a process for preparation of the composition. For example, the composition comprises a substance such as *capsicum* containing capsaicinoid components, which can include for example one or more of capsaicin, dihydro-capsaicin, and/or nor-dihydro-capsaicin, and a process for preparation of the composition, which is characterized by:
1. longer release time to prevent the release of the active ingredient in other parts of the digestive system;
2. complete intestinal absorption of the active ingredient and thereby minimize/eliminate the discomfort caused by residual unabsorbed active ingredient;
3. increased shelf life of the solid composition;
4. better taste masking for example due to presence of flavors and sugar components in the formulation and reduced irritation due to entrapment of active in matrix polymer;
5. enabling consumers to consume the active ingredients of materials without being seriously exposed to the associated disagreeable or uncomfortable odours, aromas, colours and sensory characteristics of such material at sufficiently high dosages on a regular basis through optimized formulated products.

Therefore, the main objective of the present invention is to provide a stable, free flowing, solid composition of oily, pungent, irritating, odoriferous substances which is suitable for formulating into tablets, capsules, blended powders, licaps, ointments, pastes, lotions, liniments, mouthwashes, gargles, consumable dry syrups, liquid syrups, health drinks, diet drinks, fruit juices, soft drinks and the like.

Another objective of the present invention is to provide a stable, free flowing, solid composition of oily, pungent, irritating, and odoriferous substances wherein the composition contains a weight percentage (w/w) at a range of at or about 0.1-90% of the oily, pungent, irritating and odoriferous substance of the total weight. In some embodiments, the composition contains a weight percentage (w/w) at a range of at or about 1 to 40%. In yet other embodiments, the composition contains a weight percentage (w/w) at a range of at or about 2 to 20%. It will be appreciated that the ranges above may apply to any one or more of *capsicum*, black pepper, ginger, mustard, cinnamon, garlic, onion, paprika, and/or turmeric In other examples, the composition contains a weight percentage (w/w) at a range of at or about 1-40% of the capsaicinoids, which can include for example one or more of capsaicin, dihydro-capsaicin, and/or nor-dihydro-capsaicin, as oily, pungent, irritating, and odoriferous substance. In other examples, the composition contains a weight percentage (w/w) at a range of at or about 2-20% of the capsaicinoids.

Still another objective of the present invention is to provide a stable, free flowing, solid composition of oily, pungent, irritating, odoriferous substances which facilitates extended and sustained release of the active ingredient.

Yet another objective of the present invention is to provide a stable, free flowing, solid composition of oily, pungent, irritating, odoriferous substances which has increased shelf life.

Yet another objective of the present invention is to provide a beverage grade stable, free flowing, solid composition of oily, pungent, irritating, odoriferous substances which is characterized by better taste masking due to presence of flavors and sugar components in the formulation.

Another objective of the present invention is to provide a process for preparation of stable, free flowing, solid composition of oily, pungent, irritating, odoriferous substances which are useful for fortifying aqueous/liquid systems such as foods, beverages and syrups.

Another objective of the present invention is to provide a process for preparation of stable, free flowing, solid composition of oily, pungent, irritating, odoriferous substances which can be manufactured using extrusion spheronization or inert core layering technology, such as in the production of beadlets.

The present invention has been developed in some embodiments based on the use of one or more cellulose polymers along with one or more binders. It will be appreciated that cellulosic polymers may also be used as both a binder and/or a diluent, and where the use of other suitable binders and/or diluents may also be used.

It will also be appreciated that the composition in some embodiments may also include one or more pharmaceutically acceptable excipients, such as for example but not limited to sugars and/or surfactants. It will be appreciated that polymer and excipient components such as above may be present with the active ingredient or active material such as for example in a blend, where the final composition is prepared at high shear of the blend, which can be the pressure exerted thereon, and which leads to the entrapment of the active ingredient that remarkably delays or extends the release of the active ingredient, thus reducing the pungency and irritation characteristic of the active ingredient.

It will be appreciated that the excipient(s) and/or polymer(s) used as an entrapment polymer and as a binder can be interchangeable, as well as when used as a seal coat in some circumstances. However, in a given composition, the excipient(s) and/or polymer(s) used for coating, such as for an outermost rate controlling polymer, are different from those used as entrapping and binder excipients/polymers.

In some embodiments, a further coating helps in achieving the desired complete release in the intestine and thus makes the present formulation palatable and safe for human consumption. The compositions herein are stable in the presence of accelerated stability conditions as per the International Conference on Harmonization (ICH). The resulting solid composition can be then formulated into tablets, capsules, blended powders, licaps, ointments, pastes, lotions, liniments, mouthwashes, gargles, consumable dry syrups, liquid syrups, health drinks, diet drinks, fruit juices, soft drinks and the like.

SUMMARY OF THE INVENTION

Accordingly the present invention provides an extended and sustained release stable, free flowing, solid composition of oily, pungent, irritating, odoriferous active substances. More particularly, the present invention provides an extended and sustained release stable, free flowing, solid composition of *capsicum*, extracts thereof, and/or components thereof including for example, capsaicinoids which can include for example one or more of capsaicin, dihydro-capsaicin, and/or nor-dihydro-capsaicin, and a process for preparation of the composition suitable for formulating into tablets, capsules, blended powders, licaps, ointments, pastes, lotions, liniments, mouthwashes, gargles, consumable dry syrups, liquid syrups, health drinks, diet drinks, fruit juices, soft drinks and the like.

The invention further provides a process for the preparation of the extended and sustained release stable, free flowing, solid composition of oily, pungent, irritating, odoriferous active substances.

DETAILED DESCRIPTION

Figure 1:
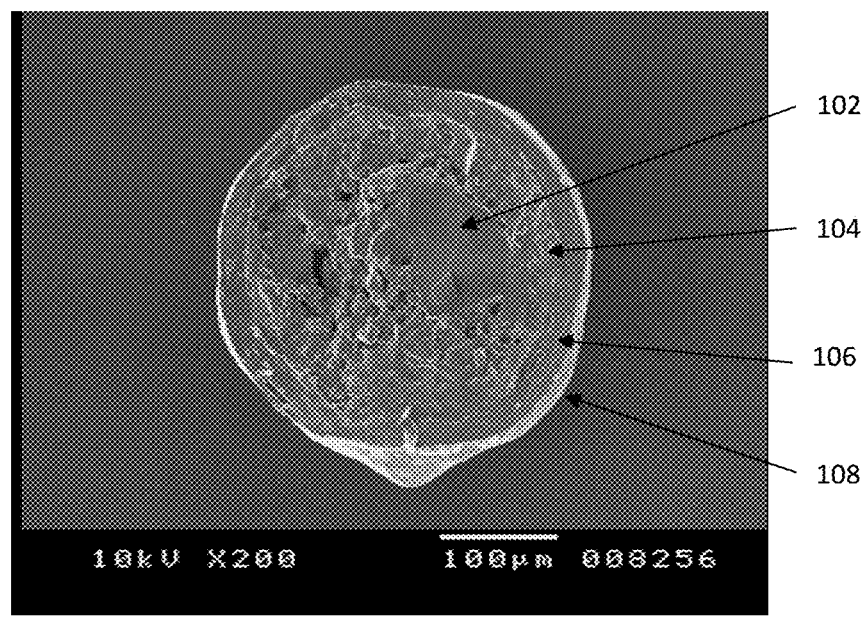
FIG. 1 is a Scanning electron microscopy (SEM) photograph of one embodiment of a composition, which is formed by a layering process resulting from Example 5.

Accordingly the present invention in some embodiments provides an extended and sustained release of a stable, free flowing, solid composition of an oily, pungent, irritating, odoriferous active substance, such as for example but not limited to *capsicum*, extracts thereof, and/or components thereof including for example, capsaicinoids which can include for example but not limited to one or more of capsaicin, dihydro-capsaicin, and/or nor-dihydro-capsaicin, which is suitable for formulating into tablets, capsules, blended powders, licaps, ointments, pastes, lotions, liniments, mouthwashes, gargles, consumable dry syrups, liquid syrups, health drinks, diet drinks, fruit juices, soft drinks and the like.

In the present invention, the pungency and the irritation characteristics of the oily natural substances is overcome by entrapping the substances in a complex formed by cellulose polymer(s) along with, in some embodiments, a combination of sugar(s), surfactant(s), binder(s) and other excipient(s) subjected to high shear.

In some embodiments, efforts are directed to reduce the manufacturing health hazards by reducing pungency, which can be achieved by preparing a composition of the oily, pungent, irritating, odoriferous active substance, such as for example including *capsicum*, a cellulosic polymer and other excipient(s) by an extrusion process.

The term 'high shear' which is meant as the pressure exerted on the components of the composition, for example when a wet mass blend of the active material and excipient (e.g. which may be prepared for example in a rapid mixer granulator using for example but not limited to a blade and chopper assembly) is forced through the mesh of an extrusion spheronizer apparatus, to obtain beadlets. The process/step of applying high shear, while forcing a wet blend through a mesh of the extrusion spheronizer apparatus helps to embed/entrap the oily, pungent, irritating, odoriferous active substance within a cellulose polymer to form a matrix.

In some embodiments, the composition can be but is not limited to being extruded by using for example any suitable extruder, such as for example but not limited to a Fuji Paudal extruder. Force excreted during this process can be measured in torque. The total torque % during this process was observed to be in a range of at or about 1.2-2.8%.

Due to the high shear, the active ingredient is entrapped which remarkably delays or extends the release of the active ingredient thus reducing the pungency and irritation characteristic of the active ingredient. The pungency can be further reduced or masked by coating the polymer entrapped substance with a polymer that can form an effective barrier between the oily, pungent, odoriferous substance and the outside environment and thus further sustains the release of the active substance and makes the present formulation palatable and safe for human consumption.

The extended and sustained release composition comprises of:
 a) a spheroidal nutrient core containing the active substance;
 b) a protective polymeric enteric coat; wherein the coating facilitates gradual and uniform release of high dosage of the active substance to reduce irritation and minimize abdominal pain and gastric discomfort associated with its release.

The oily, pungent, irritating, odoriferous active substance is at least one selected from the group consisting of *capsicum*, extracts and/or oleoresins thereof, and/or components thereof including for example, capsaicinoids which can include for example one or more of capsaicin, dihydro-capsaicin, and/or nor-dihydro-capsaicin, as well as crystals thereof; and black pepper and/or extracts thereof containing alkaloids, such as for example but not limited to piperine, isomers thereof including for example but not limited tochavicine; and ginger, oils thereof, and/or extracts thereof, any of which contain for example sesquiterpenoids, such as for example but not limited to gingerols, shagols, and/or zingerone; and mustard, oils thereof, and/or extracts thereof any of which contain fatty acids such as for example but not limited to allyl isothiocyanate and/or erucic acid; and turmeric, extracts thereof, and/oroleoresins thereof, such as for example but not limited tocurcumin, including but not limited to dessmethoxycurcumin and/or bis-desmethoxycurcumin; and cinnamon, extracts thereof, and/or oils thereof; and garlic, oils thereof, and/or extracts thereof any of which containallicin, such for example but not limited to allium, S-methyl-Lcysteine sulfoxide onion, oils thereof, and/or extracts thereof any of which contain flavinoids such as for example but not limited to quercetin; and paprika; and their chemical equivalents.

It will be appreciated that an oily, pungent, irritating, odoriferous active substance can be any substance including for example the materials listed above, which satisfies a pungency rating, which may be rated such as for example based on Scoville units. For example, pungency ratings that are at or about 50,000 to 500,000 Scoville units may be employed in the compositions herein using various oily, pungent, irritating, odoriferous active substances in suitable amounts or relative content to satisfy the pungency rating. In other embodiments, the pungency ratings of substances used in compositions herein can include an amount or relative content of the substance(s) that satisfy a pungency rating of 80,000 to 300,000 Scoville units.

Taking *capsicum* as an example, such ratings may be based on for example a commercially available *capsicum* oleoresin, which may be supplied for example at a pungency rating of about 500,000 to 1,800,000 Scoville units (e.g. using approximately 1.5 to 14% content of capsaicinoids, such as when *capsicum* is used as the active substance). In some embodiments, such as when *capsicum* is used, the relative content can be about 3.9% or greater (e.g. relative content of capsaicinoids). The above percentages refer to % w/w of actual pungent principle, e.g. capsaicinoids, in the composition. In some embodiments, the composition can contain at or about 2% content of capsaicinoids. Generally, in some embodiments, the composition can contain a range of pungency ratings using an active material (e.g. capsaicinoids) at or about 0.6 to 3.9%, and in some embodiments at or about 2%.

Following is the list of actives that may be employed in compositions herein and corresponding Scoville units thereof. It will be appreciated that suitable amounts or relative contents of these materials may be determined to meet the pungency ratings described above. For example, a relative content of any one or combination of the following pungent materials corresponding to the given Scoville units can be at or about 1.5 to 14% in any given composition herein where, in some cases, any one or more of the materials below may have comparatively lower pungency than capsaicinoids.

Gingerol—50000-100000 Scoville units
Shogol—100000-150000 Scoville units
Cinnamon oil—100000-150000 Scoville units
Piperine—100000-150000 Scoville units
Mustard oil—150000-300000 Scoville units
Garlic oil—150000-300000 Scoville units
Onion oil—150000-300000 Scoville units In some embodiments, the active substance preferably includes *capsicum* extract. The oily, pungent, irritating, odoriferous active substance used, whether the composition uses *capsicum* or not, is in the range of at or about 0.1-90% of the total weight. In other examples, the composition contains a weight percentage (w/w) at a range of at or about 1-40% of the oily, pungent, irritating, and odoriferous substance.

The cellulose containing polymers, e.g. cellulosic or cellulose polymer(s), which may be used are selected from at least one of the following examples, including but not limited to microcrystalline cellulose (MCC), Avicel® PH 101, Avicel® PH 102, Avicel® PH 103, Avicel® PH 105, Avicel® PH 112, Avicel® PH 113, Avicel® PH300, Avicel® PH212, Avicel® PH 301, Avicel® PH 302, colloidal grades of carboxymethyl cellulose sodium, hydroxypropyl methyl cellulose, methyl cellulose, hydroxyethyl cellulose, hydroxypropyl cellulose (HPC), methyl cellulose (MC), carboxymethyl cellulose (CMC), and other cellulose containing polymers, mixtures thereof, and/or various grades and viscosities thereof may be used as core polymers to entrap pungent active.

It will be appreciated that the list above can relate to core polymers, which can be used as diluents/entrapping polymer(s) as well as binder(s). Cellulose polymers such as for example, hydroxypropyl methyl cellulose (HPMC) can be used as both entrapping the active as well as for binder function. In some cases, some polymers such as MCC, for example, may not be used as both a binder and for entrapment, but may be used for entrapment or as a binder in a given composition. Other cellulose excipients in the above list may also be used as binder. It will be appreciated that binders may be used in a process of layering inert core to prepare beadlets, but may not be used in a spheronization technique for example in preparing beadlets. Use of a binder thus can be optional for extrusion spheronization. Thus for layering process, a cellulose polymer, such as HPMC, can perform both functions of entrapping pungent active as well as binding it to inert core.

It will also be appreciated that for any given composition polymers/excipients used in the core, e.g. as for entrapment and/or as a binder, are different from those used for the coating of the core, such as may be used for an outermost rate controlling polymer.

It will be appreciated that polymers used in the core and coating are different with respect to type as well as function. In some embodiments of the core, mainly cellulose type polymers, such as for example but not limited to hydroxypropyl methyl cellulose may be used to entrap active material and/or as a binder. It will be appreciated that one or more other polymers and/or excipients may also be used in the core for the entrapment of the active substance(s) in the core and/or as a binder.

Examples of other suitable binders include, but are not limited to, starch, pregelatinized starch, polyvinyl pyrrolidone (PVP), copovidone, gum acacia, xanthan gum, gum tragacanth, cellulose derivatives, such as hydroxypropylmethyl cellulose (HPMC), hydroxypropyl cellulose (HPC) and carboxymethyl cellulose (CMC) and their salts.

It will also be appreciated that the polymer used for the coating can include for example but not limited to rate controlling polymers, such as for example but not limited to shellac or dispersions thereof (e.g. an ingredient of the coating system MARCOAT™ which is a shellac dispersion, hydroxy propyl methyl cellulose phthalate (HPMCP), cellulose acetate, methacrylate polymers which are functional polymers having delayed release characteristics/pH dependent release characteristics are employed.

Further, the coating can function as a rate control or functional coating polymer, and can be selected from one or more of but not limited to methacrylates, phthalates, methyl acrylate-methacrylic acid copolymers, cellulose acetate succinate, hydroxypropyl methyl cellulose acetate succinate, polyvinyl acetate phthalate, shellac or dispersions thereof containing polymers, their derivatives, and/or mixtures thereof. It will also be appreciated that any one or more of the substances in this paragraph may be selected with one or more of the substances in the preceding paragraph.

It will also be appreciated that the polymers named above for use as a binder may also be selected for use as a seal coating in some compositions, as long as they are not used as an outermost coating, e.g. as the rate controlling coating.

For example, some seal coating polymers can be selected from at least one of Methyl Cellulose, Agar, Sodium Alginate, Hydroxy Propyl Methyl Cellulose (HPMC), Hydroxy Propyl Cellulose (HPC), Polyvinyl Pyrrolidone (PVP), Starch, Gum Arabic, Xanthan Gum, Polyethylene Glycols (PEG), preferably, Hydroxy Propyl Cellulose, Methyl Cellulose, and/or Hydroxy Propyl Methyl Cellulose, more preferably, Hydroxy Propyl Methyl Cellulose. It will be appreciated that the use of a seal coating can aid in processing for example by reducing stickiness of the surface and for application of an outer functional coat (e.g. rate-controlling coat) on a smooth surface of beadlets. It will be appreciated that the seal coat (e.g. non-functional coat) means that it does not have a role in sustaining active release from the beadlets relative to a functional coating. It will also be appreciated that any one or more of these excipients, as well as some of those listed for the binder and entrapment polymers can aid in the processing and reduce stickiness of oily pungent active layered on an inert core before applying an outer rate controlling polymer layer, so as to have uniform outer coating.

It will be appreciated that among the polymers described above, polymers for binders and polymers for seal coating can be similar when used in any particular composition. For example, polymers for binders or entrapment can include but are not limited to cellulose polymers such as MC, HPMC, HPC, MCC, PVP, starch, gums, PEG. Whereas polymers for the coating, e.g. which can include outer rate controlling coatings such as but not limited to shellac, sodium alginate, phthalates such as hypromellose phthalate (HPMCP), hypromellose acetate succinate (HPMCAS), methacrylates, cellulose acetate phthalate (CAP), and polyvinyl acetate phthalate PVAP, which are functional polymers and can control active release. It will also be appreciated that any one of these excipients can aid in the processing and reduce stickiness of oily pungent active layered on an inert core before applying outer rate controlling polymer layer, so as to have uniform outer coating.

Function of the core and coat polymers is distinctly different. Core polymer (such as MCC, HPMC) or cellulose polymers entrap the pungent active or pungent active is embedded in this matrix, so that pungency of such active is reduced and not exposed directly to gastrointestinal tract (GIT) after oral administration. It is to be appreciated that the entrapping polymer or core polymer is used for this purpose so that pungent active is entrapped/embedded to reduce or conceal its pungency. Functional polymercan beemployed as a coating polymer (e.g. rate controlling polymer), which dissolves and releases the drug at certain pH, for example to avoid the active release in stomach where the pungent active may cause irritation to delicate mucous lining. Thus by virtue of its pH dependent release characteristics, the coating polymer delays release of the pungent active and thus avoids its release in stomach, thus protecting gastric mucosa irritation by *capsicum* extract. It will be appreciated that polymers included in the list of coating polymers are of coating types which are sometimes known as enteric coating polymers, which are pH sensitive polymers that dissolve and release the active such as at alkaline pH of the intestine.

It will be appreciated that in some embodiments, polymers used for the entrapment, and for the binder in the core of the composition are different from the polymers used for the coating, e.g. outer rate controlling coating. In this regard, polymers used in the core provide a functional component of the composition, e.g. through the entrapment of the active material and then as a binder, and are different from polymers used as the coating. For example, in any given composition, polymers used for entrapment and binder are interchangeable with each other (and with seal coatings), but those used in the coating (e.g. outer rate controlling coating) of the same composition are different from those used as entrapment polymers and/or as a binder.

It will be appreciated that a seal coating may be applicable to beadlet preparation such as by an inert core layering process, but may otherwise be optional. It will be appreciated as described above, some of the entrapment polymers are interchangeable with binder excipients (such as for example HPMC) and with seal coatings. However, an excipient used for entrapment, binder, or seal coat is not employed in compositions herein as a functional rate controlling outermost coating polymer, e.g. when coating beadlets in extrusion spheronization.

Accordingly, there are two types of polymers/excipients in compositions herein.
1. Matrix and binding polymers which entrap the active material
2. Coating materials which will extend the release of active Thus it can be said that the binder in some instances is optional and is not necessary for the composition of the invention.

The sugar that may be used is selected for example from the derivatives of sugar such as Mannitol, sucrose, xylitol, sorbitol, Maltitol, Lactitol, Isomalt or mixtures thereof.

The surfactants that may be used are selected from Polysorbate, sodium lauryl sulfate, Sorbitanemonooleate, other surfactants of the same class or mixtures thereof.

In one preferred embodiment the solvent employed may be selected from Acetone, Hexane, Ethyl Acetate, Isopropyl Alcohol, Ethanol, Dichloromethane, Methanol, etc., more preferably fromAcetone, Ethanol, Dichloromethane, Isopropyl alcohol, and more preferably from Dichloro Methane and Isopropyl Alcohol.

The release of the active ingredient is not more than about 1% up to about 2 hours, not more than about 70% up to about 3 hours, more than about 90% up to about 6 hours. For example such dissolution profiles and results have been observed in capsaicin, such as in the dissolution study herein, and such results may also be applicable to other active materials described herein.

The process involves the preparation of beadlets including an oily, pungent and odoriferous substance, such as *capsicum*, by extrusion and spheronization method. In the example of *capsicum* beadlets, *capsicum* oleoresin or extract is dispersed in water to form a solution. The solution is further added to the powder blend of cellulosic polymer, sugar, surfactants, binders and other excipients. The mixing of pungent, odoriferous oil or oleoresin with the powder blend can be effected in a rapid mixing granulator and/or planetary mixer. After uniform mixing, the granules are extruded and spheronized to form uniform spheroidal beadlets. These uniform spheroidal beadlets core/spheroidal nutrient cores are further coated with polymer coating to form sustained release beadlets. The following steps provide a detailed process of the present invention.
 (i) preparing a dispersion of active substance in water and non ionic surfactants to form homogeneous dispersion.
 (ii) mixing the dispersion obtained in step (i) with cellulosic polymer along with other excipients at high shear speed of blade and chopper to form uniform matrix.
 (iii) further processing the matrix of step (ii) by extrusion and speronization to form uniform spheroidal nutrient cores.
 (iv) coating the solid spheroidal nutrient cores of step (iii) with protective polymeric enteric coat.

The temperature used in step (i) to form homogeneous dispersion is preferably in the range of about 5 deg C. to 60 deg C. and for a period in the range of about 10 min to 4 hrs.

As to the term "uniform" described above, when applied to beadlets, the term relates to size of the beadlets which is preferably within a range of at or about 100 to 2000 microns, thus having narrow size distribution, aiding free flow and efficient coating of the beadlets. When applied to a blend or mixture of the active material and excipient, such as may be prepared in a rapid mixer granulator, using chopper and blade, the term 'uniform' means that the active material is uniformly mixed with cellulose polymer and other excipient(s), so as to prepare the matrix which exhibits content uniformity (if any part of blend is withdrawn as sample, the content of the active material will be about the same. Thus, the active material can be evenly or homogenously distributed throughout the matrix.

The spheroidal nutrient core of step (iii) has a diameter of about 100 microns to 2000 microns. In some embodiments, the diameter is about 100 microns to about 1000 microns.

The organic solvent is selected from a group consisting of Dichloromethane (DCM), Ethyl acetate, Acetone, Isopropanol (IPA), Ethanol.

The protective polymeric enteric coating comprises of titanium dioxide, purified talc, an additional polymer for gradual release and a soothing agent.

The temperature used in step (iv) preferably ranges from about 20 deg C. to 55 deg C.

The final formulation obtained has a diameter of about 210 microns to 707 microns.

The extrudes were spheronized at a pitch plate speed of about 500 to 1700 rpm.

The process is carried out by using rapid mixing granulator and/or planetary mixer.

The process for coating the spheroidal solid composition of step (iii) with the protective polymer is carried out by using bottom spray and/or tangential spray and/or top spray coating and/or Flex stream granulator.

The composition is stable and free flowing.

Scanning electron microscopy (SEM) photographs show two layers for beadlets prepared by extrusion spheronization method, which employs high shear to promote the entrapment of the active ingredient. These show that cellulose polymers (MCC as well as binder) are present in close vicinity of the active; while functional delayed release polymer is present as distinct outer layer on the periphery. Preparation conditions at high shear results in good entrapment of the active material, such as in a cellulose polymer matrix.

Figure 2:
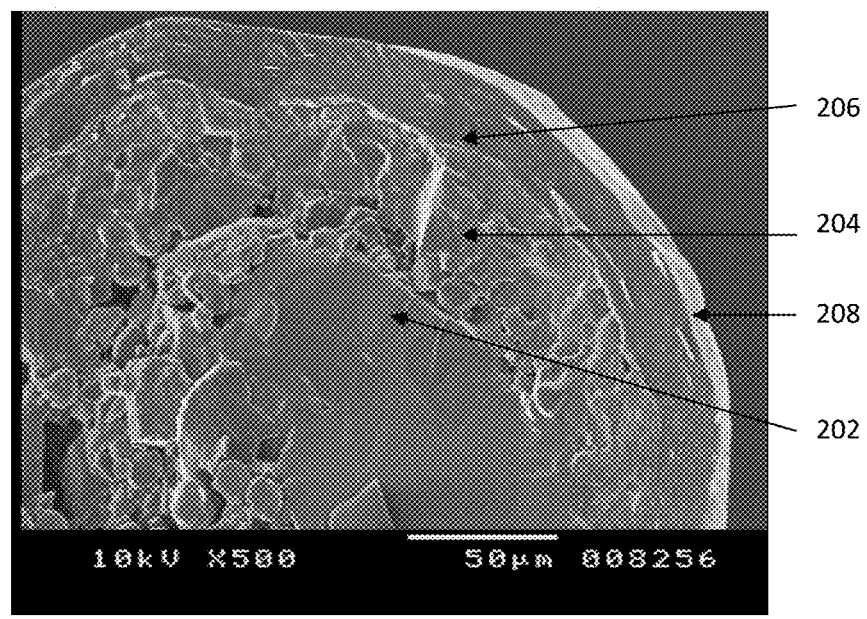
FIG. 2 is a SEM photograph of one embodiment of a composition, which is formed by a layering process resulting from Example 5.
Figure 3:
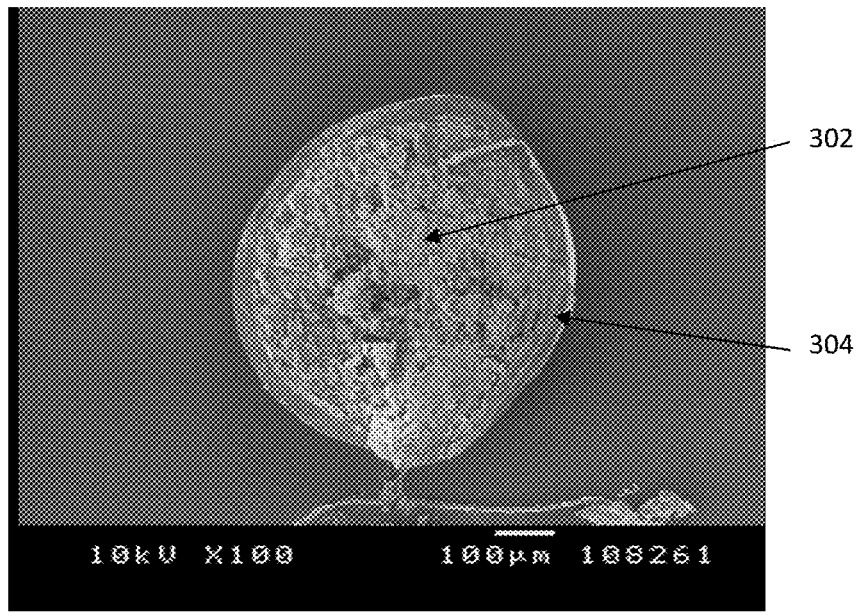
FIG. 3 is a SEM photograph of one embodiment of a composition herein, which is formed by extrusion spheronization resulting from Example 2.
Figure 4:
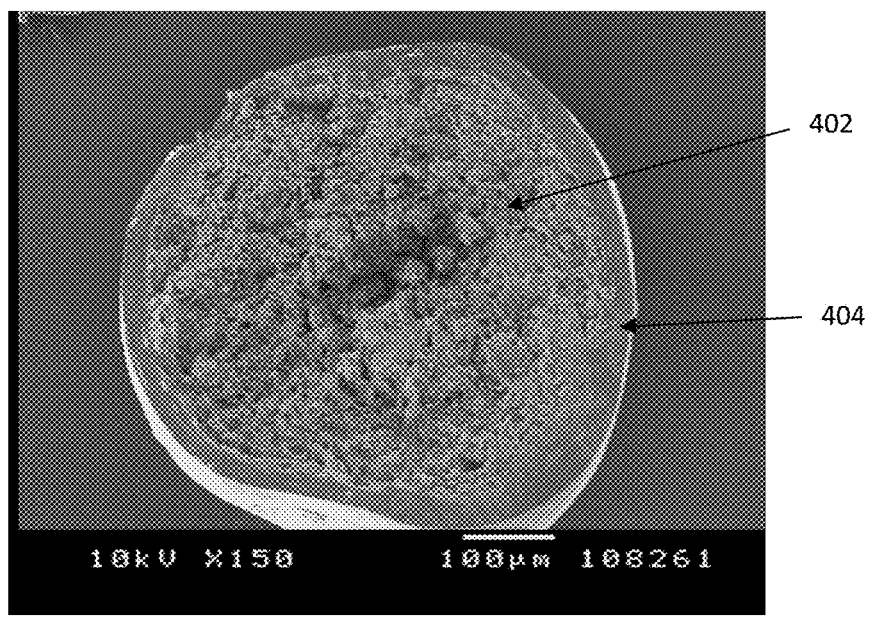
FIG. 4 is a SEM photograph of one embodiment of a composition herein, which is formed by extrusion spheronization resulting from Example 2.
Figure 5:
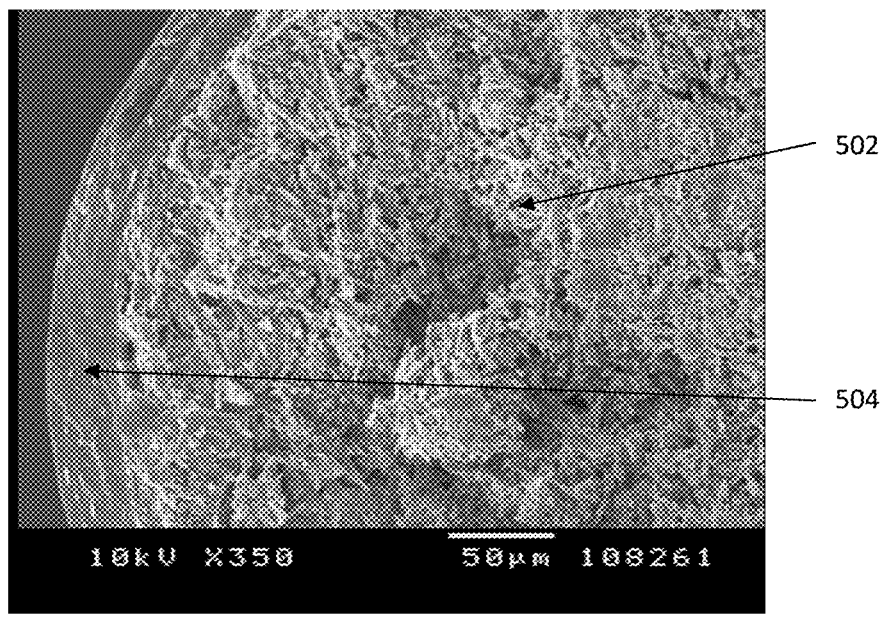
FIG. 5 is a SEM photograph of one embodiment of a composition herein, which is formed by extrusion spheronization resulting from Example 2.

FIGS. 1 to 5 are examples of SEM photographs of compositions to showcompositions made by a layer process (e.g. FIGS. 1 and 2) relative to those made by the extrusion spheronization method having the components described herein and where the active material is entrapped in cellulose polymer (e.g. FIGS. 3 to 5). The SEM photographs of FIGS. 1 and 2 are results according Example 5 which is further described below, and the SEM photographs of FIGS. 3 to 5 are results from Example 2 which is further described below.

In FIGS. 1 to 5, the cross-section morphologies were visualized using Scanning Electron Microscope (JSM-5400, JEOL, Japan). The samples were mounted on a brass stub using double sided tape and then sputtered with a thin layer of gold using Sputter coater (JEOL-JEC550-twin coater, Japan). The photographs were taken at an acceleration voltage of 10 kV.

FIGS. 1 and 2 show SEM images of compositions herein which are formed into beadlets (e.g. prepared by a layering process). In FIG. 1, the cross section of a beadlet clearly shows the adsorption of active material in the excipient matrix on the inert core sugar spheres followed by several functional coating (shown as 108).
 1. Inert core (Sugar spheres) (shown as 102)
 2. Active and excipients matrix (shown as 104)

Polymer seal coating (shown as 106) is also shown, where this layer is specific to beadlets produced by the layering process, wherein it is used to reduce sticky outer surface of the core due to oleoresin, and to ease the handling and further coating of beadlets. Cellulose polymers are used in this seal coating and the % weight gain of the polymer coat is much less, as it is generally a non-functional coat, which is used in this example to aid processing and apply the outer functional coat 108 on smooth surface of beadlets. It will be appreciated that the non-functional coat 106 means that it does not have a role in sustaining active release from the beadletsrelative to the functional coating 108, thus can be called a non-functional.

In FIG. 2, the cross section of a beadlet clearly shows the adsorption (evenly dispersed/distributed in matrix of excipient) of active material in the excipient matrix on the inert core sugar spheres followed by several functional coatings.
 1. Inert core (Sugar spheres) (shown as 202)
 2. Active and excipients matrix (shown as 204)
 3. Polymer seal coating (shown as 206)
 4. Functional coating (shown as 208)

SEM images of beadlets made by the extrusion & spheronization process (e.g. at high shear are shown in FIGS. 3 to 5.

In FIG. 3, the cross section of a beadlet clearly shows the formation of active material and excipients matrix at the center and also showing the functional coating.
 1. Active and excipients matrix (shown as 302)
 2. Functional coating (shown as 304)

In FIG. 4, the cross section of a beadlet clearly shows the formation of active material and excipient matrix at the center and also showing the functional coating.
 1. Active and excipients matrix (shown as 402)
 2. Functional coating (shown as 404)

In FIG. 5, the cross section of a beadlet clearly shows the formation of active material and excipients matrix at the center and also showing the functional coating.
 1. Active and excipients matrix (shown as 502)
 2. Functional coating (shown as 504)

The beadlets herein can be further formulated into tablets, capsules, blended powders, licaps, ointments, pastes, lotions, liniments, mouthwashes, gargles, consumable dry syrups, tablets, capsules, liquid syrups, health drinks, diet drinks, fruit juices, soft drinks and the like.

The details of the present invention are described in the Examples given below which are provided to illustrate the invention and therefore should not be construed to limit the scope of the present invention.

It is to be appreciated that in some examples, entrapment polymer and binder are used interchangeably, where HPMC is just one example which can be used for entrapment as well as a binder excipient, and where there may be differences in the grade used, and based upon its application with respect to viscosity. For example HPMC E-15 has a viscosity around 15 Cp and may be used as diluents for entrapment, while Methocel VLV has viscosity about 5 Cp and may be used as binder. See e.g. Example 1 further described below, wherein MCC and HPMC is used for entrapment, where HPMC of a different grade is used as binder in the same formula. See also e.g. Examples 2 to 4, where MCC is used for entrapment and HPMC is used as binder, and e.g. Examples 5 and 6 show beadlet preparationsby a layering process, wherein no entrapment excipient is required, but HPMC is used as a binder. The examples are further described as follows.

EXAMPLES

Examples 1-6 represent a process for preparation of *capsicum* beadlets by extrusion and spheronization method. *Capsicum* oleoresin is dispersed in water under stirring to form a dark brownish to black solution. The solution is added slowly and in a continuous manner to a powder blend of cellulose, Mannitol, Tween 80 and other excipients in a planetary mixer, at a speed of about 5-25 rpm/min, where the same procedure can be carried out by using rapid mixing granulator such as at the following parameters—Impeller speed between about 750-1500 rpm/min and chopper speed is between about 1440-2800 rpm/min. After uniform mixing the granules are added to an extruder; which can be carried out either by using a single and/or a twin Screw extruder. The extrusion process is carried out at a speed of about 20-44 rpm/min, extrudes are further spheronized by using about 0.5 mm Chequered plate, initially spheronization is carried out at a slow speed of about 500-750 rmp/min for about 1-2 min followed by increase in speed up to about 1500 rpm/min. *Capsicum* oleoresin beadlets are dried in a tray dryer at about 40-50° C. for about 20-30 min.

The *Capsicum* oleoresin beadlets are further coated with a functional rate controlling polymer by using fluid-bed system with bottom spray mechanism at inlet temperature of 35 to 55° C., spray rate of 10 g/hour to about 600 g/hour and atomization pressure in the range of about 0.1 kg/cm2 to about 3 kg/cm2. After completion of the coating process the beadlets are dried at a temperature of 40° C. for 30 min.

| Sr. No | Ingredients | 1 | 2 | 3 % W/W | 4 | 5 | 6 |
|---|---|---|---|---|---|---|---|
| 1 | Capsicum oleoresin | 8.6 | 8.3 | 8.3 | 8.3 | 8.3 | 8.3 |
| 2 | NPS (Sugar) | 0 | 0 | 0 | 0 | 39.9 | 80 |
| 3 | HPMC-E15 | 4.3 | 0 | 0 | 0 | 0 | 0 |
| 4 | SSG | 7 | 8 | 8 | 8 | 8 | 0 |
| 5 | MCC PH 101 | 69.6 | 40.3 | 39.9 | 32.6 | 0 | 0 |
| 6 | Talc | 9.9 | 0 | 0 | 0 | 0 | 0 |
| 7 | Mannitol | 0 | 40.6 | 39.9 | 46.6 | 39.9 | 9.1 |
| 8 | Methocel VLV | 0 | 0.7 | 0.7 | 0.7 | 0.7 | 0.7 |

-continued

| Sr. No | Ingredients | 1 | 2 | 3 % W/W | 4 | 5 | 6 |
|---|---|---|---|---|---|---|---|
| 9 | Tween 80 | 0 | 1.7 | 2.7 | 3.3 | 0 | 0 |
| 10 | Sodium Docusate | 0 | 0 | 0 | 0 | 0 | 0 |
| 11 | MARCOAT ™ | 1.8 | 1.8 | 1.8 | 1.8 | 1.8 | 1.8 |
| 12 | Purified talc | 0 | 0 | 0 | 0 | 0 | 0 |
| 13 | Titanium dioxide | 0.1 | 0.1 | 0.1 | 0.1 | 0.1 | 0.1 |
| | Total | 100 | 100 | 100 | 100 | 100 | 100 |

Stability Data

The *Capsicum* compositions of Examples 1, 2, 3, and 4 were subjected to accelerated stability studies as per ICH guidelines at 40±2° C./75±5% RH. The result of the study were as follows,

| | | (Total capsaicinoids content %) | | |
|---|---|---|---|---|
| Sr. No. | Example No | Initial Assay | After 6 months 40 ± 2° C./75 ± 5% RH | % loss |
| 1 | 1 | 2.3 | 2.29 | 0.43 |
| 2 | 2 | 2.33 | 2.31 | 0.85 |
| 3 | 3 | 2.28 | 2.27 | 0.43 |
| 4 | 4 | 2.39 | 2.35 | 1.67 |

Conclusion:

The 3 months stability data at 40° C. and 75% RH was found satisfactory for assay and dissolution.

Dissolution Data

| Dissolution Study of Beadlets | | | | | |
|---|---|---|---|---|---|
| | | RPM: –125 % Release | | | |
| Apparatus USP Type-I | | Example | Example | Example | Example |
| Medium | Time | No. 1 | No. 2 | No. 3 | No. 4 |
| 1N hydrochloric acid solution | 0 h | 0.00 | 0.00 | 0.00 | 0.00 |
| | 1 h | 0.00 | 0.00 | 0.00 | 0.00 |
| | 2 h | 0.00 | 0.00 | 0.00 | 0.00 |
| Phosphate buffer pH 7.4 with SLS 0.5% | 3 h | 68.06 | 63.48 | 61.10 | 64.50 |
| | 4 h | 92.87 | 92.79 | 92.18 | 91.20 |
| | 5 h | 95.18 | 94.24 | 93.91 | 93.24 |
| | 6 h | 96.98 | 96.40 | 96.04 | 96.57 |

Conclusion:

The dissolution study did not show any release of capsaicinoids in 0.1 N HCl within 2 hours and there was complete release of capsaicinoids in phosphate buffer pH 7.4 with SLS within a 6 hour time period.

ADVANTAGES OF THE INVENTION

1. Provides a free flowing, non-sticky solid composition of oily, pungent, irritating, odoriferous active substances, in which the inherent nutritional and biological benefits of the active substance is retained with high concentration but without the associated discomfort of the active substance, andin which the composition is suitable for subsequent formulation into consumable dry syrups, liquid syrups, health drinks, diet drinks, fruit juices, soft drinks and the like which are useful in reduction of body weight. For example, associated discomfort of an oily, pungent, irritating, odoriferous active substance is taken care of by embedding it in cellulose polymer in the core of a beadlet composition, and by an extrusion spheronization method, wherein high shear is applied while preparing beadlets. Further, even though oleoresin may be used, the composition is non-sticky as an extrusion method is used for entrapping oily active in the matrix of the core.

2. The product is an extended and sustained delivery product which facilitates gradual release of the dosage in the intestine without causing irritation/discomfort in the mouth, esophagus or stomach. For example, specific coating polymers are used which are functional, e.g. for entrapment of the active substance in the core, and are used for control of active release which are responsible for extended active release.

3. Provides the products in a user-friendly form which does not cause skin irritation or pungency during tableting or capsule-filling. For example, the composition and process herein both help to avoid irritation, while formulation as well as to patients after administration.

4. Provides a free flowing solid composition of oily, pungent, irritating odoriferous substances which has a high bulk density (i.e. consistently higher than about 0.5 g/ml, and preferably in the range >0.60 g/ml) high bulk density (e.g. >0.60 g/ml).

5. Provides novel free flowing solid compositions of oily, pungent, irritating and odoriferous substances wherein the composition contains 0.1-90% of the oily pungent and odoriferous substance.

6. Protects the oily, pungent, irritating, odoriferous substances from environmental factors such as light, oxygen & heat.

7. Retains the volatile materials present in the oily, pungent, irritating, odoriferous substances.

8. Retains the inherent beneficial nutritional and biological benefits through an appropriately high concentration of the active volatile and oily active ingredient, without the associated discomfort and disadvantages experienced in industrial use or in regular consumption. For example, both core and coat structural components are responsible for these characteristics of the resultant composition.

9. Provides a convenient means of delivering highly pungent, irritating and odoriferous substances such *capsicum* extract, garlic oil, fish oils, spice oils and extracts, herb oils and extracts in high doses by oral route. For example, both core and coat structural components are responsible for these characteristics of the resultant composition.

Aspects

It will be appreciated that any one or more of the following aspects 1 to 18 may be combined with any of the following aspects 19 to 21.

1. A composition suitable for extended and sustained release, comprising an oily, pungent, irritating, odoriferous active substance, wherein the composition is suitable for subsequent formulation into one or more of tablets, capsules, blended powders, licaps, ointments, pastes, lotions, liniments, mouthwashes, gargles, consumable dry syrups, liquid syrups, health drinks, diet drinks, fruit juices, and soft drinks 2. The composition as in aspect 1, wherein the active substance is a component of a beadlet formulation, the beadlet formulation comprising the active substance present with one or more polymers as a matrix and a functional coating surrounding the matrix.

3. The composition as in aspect 2, further comprising a seal coating between the matrix and the functional coating, and an inert core inside the matrix.

4. The composition as in any of aspects 1 to 3, comprising:
   c) a spheroidal nutrient core containing the active substance;
   d) a polymeric enteric coat; wherein the coating facilitates gradual and uniform release of high dosage of the active substance to reduce irritation and minimize abdominal pain and gastric discomfort associated with its release.

5. The composition as in any of aspects 1 to 4, wherein the active substance is 0.1-90% by weight of the total weight of the composition.

6. The composition as in aspect 4 or 5, wherein the spheroidal nutrient core containing active substance further contains one or more cellulose containing polymers.

7. The composition as in any of aspects 4 to 6, wherein the spheroidal nutrient core containing active substance further contains one or more of sugar and starch.

8. The composition as in any of aspects 4 to 7, wherein the spheroidal nutrient core containing active substance further contains a surfactant.

9. The composition as in any of aspects 1 to 8, wherein the active ingredient is configured within the composition to be released at a rate of not more than 1% up to 2 hours, not more than 70% up to 3 hours, more than 90% up to 6 hours.

10. The composition as in any of aspects 1 to 9, wherein the active substance is selected from at least one of the group consisting of *capsicum* extract; *capsicum* oleoresin; capsaicin crystals; black pepper, ginger, garlic, mustard, turmeric oleoresin, cinnamon, and paprika.

11. The composition as in any of aspects 1 to 10, wherein active substance is *capsicum* extract.

12. The composition as in any of aspects 6 to 10, wherein the cellulose containing polymer is selected from at least one of the group consisting of microcrystalline cellulose, colloidal grades carboxymethyl cellulose sodium, hydroxypropyl methyl cellulose, and mixtures thereof 13. The composition as in any of aspects 7 to 12, wherein the sugar is selected from at least one of mannitol, sucrose, xylitol, sorbitol, maltitol, lactitol, isomalt, and mixtures thereof.

14. The composition as in any of aspects 8 to 13, wherein the surfactant used are selected from at least one of the group consisting of polysorbate, sodium lauryl sulfate, sorbitan monooleate, and mixtures thereof 15. The composition as in any of aspects 4 to 14, wherein the polymeric enteric coat comprises one or more of titanium dioxide and talc.

16. The composition as in any of aspects 4 to 15, wherein the polymeric enteric coat comprises a soothing agent, the soothing agent includes menthol or peppermint.

17. The composition as in any of aspects 4 to 16, wherein the polymeric enteric coat includes a rate controlling functional coating selected from at least one of the group consisting of hydroxy propyl methyl cellulose acetate phthalate, hydroxypropyl methyl cellulose phthalate, methacrylates, phthalate methyl acrylate-methacrylic acid copolymers, cellulose acetate succinate, polyvinyl acetate phthalate, and a shellac dispersion containing polymers, and mixtures thereof.

18. The composition as in any of aspects 1 to 17, wherein the composition is free flowing and stable.

19. A process for preparation of an extended and sustained release composition of oily, pungent, irritating, odoriferous active substance, comprising:
(i) preparing a dispersion of an oily, pungent, irritating, odoriferous active substance in water and non-ionic surfactants;
(ii) mixing the dispersion obtained in step (i) with one or more cellulosic polymers along with other excipients including one or more of sugar and starch to form a uniform matrix;
(iii) further processing the matrix of step (ii) by extrusion and spheronization to form a uniform spheroidal nutrient core; and
(iv) coating the spheroidal nutrient core of step (iii) with a rate controlling enteric polymeric coat.

20. The process as in aspect 19, wherein step (ii) is carried out by using rapid mixing granulator and/or planetary mixer.

21. The process as in aspect 19 or 21, wherein step (iv) is carried out by using one or more of a bottom spray, a tangential spray, a top spray coating, and a flex stream granulator.

We claim:

1. A composition suitable for delayed, extended and sustained release, comprising:
a spheroidal nutrient core including an oily, pungent, and odoriferous active substance, a cellulose containing polymer, one or more of sugar and starch and an excipient,
wherein the oily, pungent, and odoriferous active substance is *capsicum* oleoresin and has a pungency rating of about 50,000 to 1,800,000 Scoville units,
wherein the cellulose containing polymer is at least one selected from the group consisting of microcrystalline cellulose, colloidal grades carboxymethyl cellulose sodium, and hydroxypropyl methyl cellulose,
wherein the sugar is at least one selected from the group consisting of mannitol, sucrose, xylitol, sorbitol, maltitol, lactitol, and isomalt,
wherein the excipient includes a binder, wherein the binder is at least one selected from the group consisting of starch, pregelatinized starch, polyvinyl pyrrolidone (PVP), copovidone, gum acacia, xanthan gum, gum tragacanth, hydroxypropylmethyl cellulose (HPMC) and a salt thereof, hydroxypropyl cellulose (HPC) and a salt thereof, and carboxymethyl cellulose (CMC) and a salt thereof,
the active substance, the at least one cellulose containing polymer, and the excipient being formed as a matrix, where the active substance is entrapped by the at least one cellulose containing polymer, so as to reduce or conceal a pungency and/or odor of the active substance and to provide delayed and then extended and sustained release of the active substance upon dissolution, where entrapment of the active substance is obtained by extrusion spheronization,
the matrix including the active substance being uniformly mixed with the at least one cellulose containing polymer,
the at least one cellulose containing polymer having a higher viscosity than that of the binder; and
an outer enteric polymeric coating that coats the spheroidal nutrient core, the outer enteric polymeric coating to facilitate delayed and gradual release of the active substance, and the outer enteric polymeric coating being different from the at least one cellulose containing polymer,
wherein the outer enteric polymeric coating is at least one selected from the group consisting of hydroxypropyl methyl cellulose acetate phthalate, hydroxypropyl methyl cellulose phthalate, methacrylate, phthalate methyl acrylate-methacrylic acid copolymer, cellulose acetate succinate, polyvinyl acetate phthalate, and a shellac dispersion containing polymer, and
wherein the active substance is configured within the composition to be released at a rate of not more than 1% up to 2 hours, more than 75% in 4 hours, more than 90% up to 6 hours.

2. The composition as claimed in claim 1, further comprising a seal coating between the matrix and the outer enteric polymeric coating, and an inert core inside the matrix.

3. The composition as claimed in claim 1, wherein the active substance is 0.1-90% by weight of the total weight of the composition.

4. The composition as claimed in claim 1, wherein the spheroidal nutrient core further contains a surfactant.

5. The composition as claimed in claim 4, wherein the surfactant used is selected from at least one of the group consisting of polysorbate, sodium lauryl sulfate, sorbitan monooleate, and mixtures thereof.

6. The composition as claimed in claim 1, wherein the outer enteric polymeric coating comprises one or more of titanium dioxide and talc.

7. The composition as claimed in claim 1, wherein the outer enteric polymeric coating comprises a soothing agent, the soothing agent includes menthol or peppermint.

8. The composition as claimed in claim 1, wherein the composition is free flowing and stable.

9. A process for preparation of a composition suitable for delayed, extended and sustained release as claimed in claim 1, comprising:
(i) preparing a dispersion of an oily, pungent, irritating, odoriferous active substance in water and non-ionic surfactants, wherein the oily, pungent, and odoriferous active substance is *capsicum* oleoresin and has a pungency rating of about 50,000 to 1,800,000 Scoville units;
(ii) mixing the dispersion obtained in step (i) with one or more cellulosic polymers, one or more of sugar and starch and an excipient, the excipient including a binder, wherein the binder is at least one selected from the group consisting of starch, pregelatinized starch, polyvinyl pyrrolidone (PVP), copovidone, gum acacia, xanthan gum, gum tragacanth, hydroxypropylmethyl cellulose (HPMC) and a salt thereof, hydroxypropyl cellulose (HPC) and a salt thereof, and carboxymethyl cellulose (CMC) and a salt thereof, and wherein the one or more sugar is at least one selected from the group consisting of mannitol, sucrose, xylitol, sorbitol, maltitol, lactitol, and isomalt,
the active substance, the one or more cellulosic polymers, and the excipient being formed as a matrix where the active substance is entrapped by the one or more cellulosic polymers, so as to reduce or conceal a pungency and/or odor of the active substance and to provide delayed, extended and sustained release of the active substance upon dissolution, the matrix including the active substance being uniformly mixed with the one or more cellulosic polymers, the one or more cellulosic polymers having a higher viscosity than the binder;

(iii) further processing the matrix of step (ii) by extrusion and spheronization to form a uniform spheroidal nutrient core; and (iv) coating the spheroidal nutrient core of step (iii) with an outer enteric polymeric coating, the outer enteric polymeric coating being different from the one or more cellulosic polymers, wherein the outer enteric polymeric coating is at least one selected from the group consisting of hydroxypropyl methyl cellulose acetate phthalate, hydroxypropyl methyl cellulose phthalate, methacrylate, phthalate methyl acrylate-methacrylic acid copolymer, cellulose acetate succinate, polyvinyl acetate phthalate, and a shellac dispersion containing polymer, and wherein the active substance is configured within the composition to be released at a rate of not more than 1% up to 2 hours, more than 75% in 4 hours, more than 90% up to 6 hours.

10. The process as claimed in claim 9, wherein step (ii) is carried out by using rapid mixing granulator and/or planetary mixer.

11. The process as claimed in claim 9, wherein step (iv) is carried out by using one or more of a bottom spray, a tangential spray, a top spray coating, and a flex stream granulator.

* * * * *